(12) United States Patent
Meyer, Jr.

(10) Patent No.: US 9,247,909 B2
(45) Date of Patent: Feb. 2, 2016

(54) LUMEN BASED PRESSURE SENSING GUIDEWIRE SYSTEM WITH DISTORTION CORRECTION

(75) Inventor: Douglas E. Meyer, Jr., Folsom, CA (US)

(73) Assignee: Volcano Corporation, San Diego, CA (US)

( * ) Notice: Subject to any disclaimer, the term of this patent is extended or adjusted under 35 U.S.C. 154(b) by 732 days.

(21) Appl. No.: 13/339,920

(22) Filed: Dec. 29, 2011

(65) Prior Publication Data
US 2012/0172732 A1 Jul. 5, 2012

Related U.S. Application Data

(60) Provisional application No. 61/429,026, filed on Dec. 31, 2010.

(51) Int. Cl.
| A61B 5/02 | (2006.01) |
| A61B 5/00 | (2006.01) |
| A61B 5/0215 | (2006.01) |

(52) U.S. Cl.
CPC ........... *A61B 5/6851* (2013.01); *A61B 5/02156* (2013.01); *A61B 5/7257* (2013.01)

(58) Field of Classification Search
None
See application file for complete search history.

(56) References Cited

U.S. PATENT DOCUMENTS

| 3,811,427 | A | * | 5/1974 | Kresse | 600/488 |
| 4,282,881 | A | * | 8/1981 | Todd et al. | 600/487 |
| 4,456,013 | A | * | 6/1984 | De Rossi et al. | 600/488 |
| RE31,873 | E | * | 4/1985 | Howes | 600/487 |
| 4,809,709 | A | * | 3/1989 | Brooks | 600/561 |
| 4,850,358 | A | * | 7/1989 | Millar | 600/486 |
| 4,928,693 | A | * | 5/1990 | Goodin et al. | 600/434 |
| 5,018,529 | A | * | 5/1991 | Tenerz et al. | 600/480 |
| 5,178,159 | A | * | 1/1993 | Christian | 600/585 |
| 5,313,957 | A | * | 5/1994 | Little | 600/561 |
| 5,425,371 | A | * | 6/1995 | Mischenko | 73/705 |
| 5,450,853 | A | * | 9/1995 | Hastings et al. | 600/488 |
| 5,715,827 | A | * | 2/1998 | Corl et al. | 600/486 |
| 5,964,714 | A | * | 10/1999 | Lafontaine | 600/561 |
| 6,106,476 | A | * | 8/2000 | Corl et al. | 600/486 |
| 6,106,477 | A | * | 8/2000 | Miesel et al. | 600/486 |
| 6,394,986 | B1 | * | 5/2002 | Millar | 604/264 |
| 6,974,422 | B1 | * | 12/2005 | Millar | 600/561 |

(Continued)

OTHER PUBLICATIONS

International Search Report and Written Opinion received in corresponding Patent Cooperation Treaty Application No. PCT/US2011/067751, dated Jun. 26, 2012, 8 pages.

*Primary Examiner* — Jacqueline Cheng
*Assistant Examiner* — Eric Messersmith
(74) *Attorney, Agent, or Firm* — Haynes and Boone, LLP (57) ABSTRACT

A guidewire is disclosed that is constructed using tubular members that create a hollow lumen that runs from the proximal end of the guidewire to a window towards the distal end of the wire. This internal lumen is filled with a fluid that allows pressure exerted at the window to exert pressure at the proximal end of the guide wire proportional to the pressure exerted at the window. This pressure exerted at the proximal end of the guidewire is measured using a pressure transducer external of the guidewire. The pressure transducer converts the measured pressure into an electrical signal that is proportional to the pressure at the window. The electrical signal is manipulated to correct for errors that are due to the pressure signal traveling though the inner lumen of the guidewire to ensure the electrical signal matches the pressure exerted at the window.

14 Claims, 4 Drawing Sheets

(56) References Cited

U.S. PATENT DOCUMENTS

| | | | |
|---|---|---|---|
| 6,994,695 B1* | 2/2006 | Millar | 604/264 |
| 7,097,620 B2* | 8/2006 | Corl et al. | 600/486 |
| 7,731,664 B1* | 6/2010 | Millar | 600/488 |
| 2002/0007125 A1* | 1/2002 | Hickey | 600/486 |
| 2002/0065472 A1 | 5/2002 | Brockway et al. | |
| 2003/0018273 A1* | 1/2003 | Corl et al. | 600/486 |
| 2007/0124127 A1* | 5/2007 | Danehorn et al. | 703/11 |
| 2007/0168145 A1 | 7/2007 | Beyer et al. | |
| 2008/0077021 A1 | 3/2008 | Ferber et al. | |
| 2008/0255466 A1 | 10/2008 | Wellnhofer | |
| 2010/0113939 A1* | 5/2010 | Mashimo et al. | 600/470 |
| 2010/0113943 A1* | 5/2010 | Burnes et al. | 600/486 |
| 2011/0092828 A1* | 4/2011 | Spohn et al. | 600/485 |
| 2013/0030300 A1* | 1/2013 | Ahmed et al. | 600/454 |
| 2013/0237864 A1* | 9/2013 | Mazar et al. | 600/488 |
| 2013/0274619 A1* | 10/2013 | Stone et al. | 600/488 |
| 2014/0024956 A1* | 1/2014 | Purdy et al. | 600/488 |

\* cited by examiner

LUMEN BASED PRESSURE SENSING GUIDEWIRE SYSTEM WITH DISTORTION CORRECTION

CROSS-REFERENCE TO RELATED APPLICATIONS

This application claims priority to and the benefits of U.S. Provisional Patent Application No. 61/429,026, filed on Dec. 31, 2010, which is hereby incorporated by reference in its entirety.

BACKGROUND OF THE INVENTION

1. Field of the Invention

The present invention relates generally to the field of guidewires used to diagnose and treat maladies in humans and more specifically to pressure-sensing guidewires used in intravascular procedures.

2. Description of the Related Art

It is often desirable to determine the severity of a stenosis or occlusion in the coronary arteries by measuring the pressure distally and proximally of the stenosis or occlusion. Devices today that are used for this purpose include catheter like members with some type of pressure-sensing device incorporated therein. Such devices are often referred to as a pressure-sensing guidewire since they can provide the dual function of guidewire and a pressure measuring device. Many of these devices today are constructed by incorporating a piezo-resistive pressure sensing device towards the distal end of a hollow guidewire body. Three electrical wires are then run the length of the hollow guidewire in order to connect the piezo-resistive pressure sensing device to the proper measurement instrumentation.

One problem associated with the currently available pressure-sensing guidewires is the cost to manufacturer such a device. These devices can be up to 10 times more expensive to manufacturer than a standard guidewire and up to 20 times more expensive than a standard catheter with invasive blood pressure sensor. The main reason for the high cost is the piezo-resistive device itself and the labor required to run electrical wires through the length of guidewire and terminate them on the proximal end of the wire. Thus adoption of the current pressure-sensing guidewires by medical professionals is inhibited due to the large cost difference between these devices and standard guidewires.

A second problem associated with the currently available pressure-sensing guidewires is that the accuracy of the piezo-resistive pressure sensor inside the guidewire is not as accurate as a standard invasive blood pressure sensor. Due to limited space inside the guidewire, the piezo-resistive pressure senor must use a half bridge design in order to minimize the number of electrical wires that must be run the length of the guidewire. As a result, the currently available pressure sensing guidewires have reduced zero drift stability and increased susceptibility to thermal variations over standard full bridge invasive blood pressure sensors.

A third problem associated with the currently available pressure-sensing guidewires is reliability of such devices. These devices have electrical wires running the length of the guidewire that terminate to the piezo-resistive sensor on the distal end and to an electrical connector on the proximal end. These electrical connections must be sealed from the surrounding fluid in the body and any tiny breach will cause errors in the pressure measurement. As a result, there is high rate of failure with such a device because of the number of electrical interconnects and their proximity to fluids.

A guidewire with a single fluid filled lumen from the distal end to the proximal end, with a pressure transducer attached at the proximal end would solve the three problems mentioned above because it does not require electrical wires to run the length of the guidewire 10 and a full bridge, low cost pressure transducer can be used at the proximal end of the wire. However measuring pressure through a fluid filled tube creates distortions in the pressure waveform that creates measurement error because the pressure exerted on one end of the tube is no longer directly proportional to the pressure measured on the other end of the tube. In order to accurately measure pressure through a fluid filled tube, these distortions created by the fluid filled tube must be corrected for.

Figure 1:
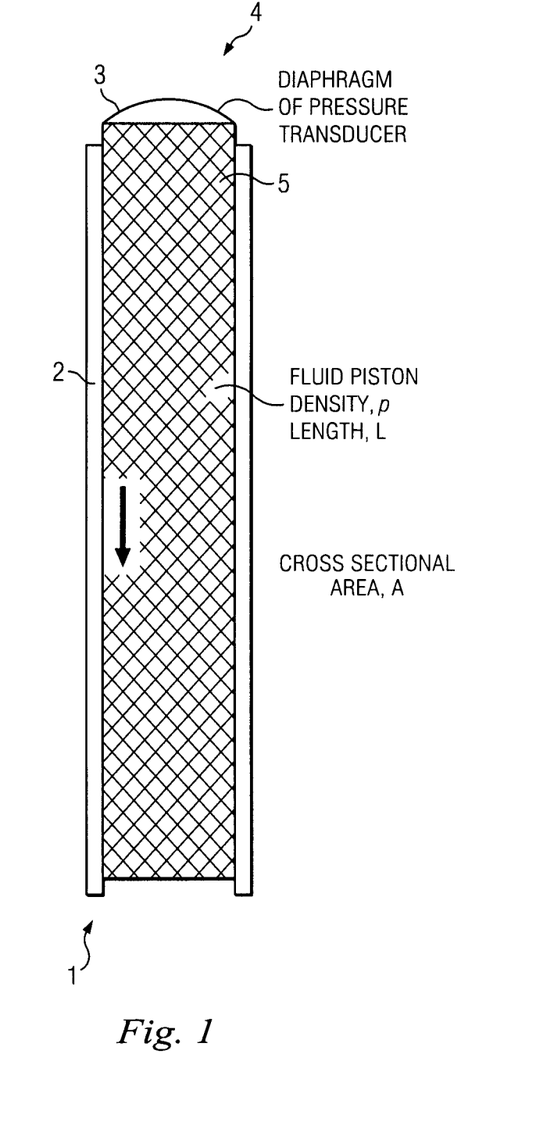
FIG. 1 is a schematic view of the elements related to determining pressure in a tube.

As shown in FIG. 1, when pressure is applied to one end 1 of a fluid filled tube 2 having a pressure transducer 3 on the other end 4 of the tube 2 the relationship between pressure p(t) and an electrical output E of the pressure transducer 3 is governed by the following differential equation:

$$\ddot{E} + \frac{c}{\rho LA}\dot{E} + \frac{k}{\rho LA}E = \frac{K}{\rho L}p(t)$$

where $\rho$ is the density of the fluid 5 in the tube 2, L is the length of the tube 2, A is the cross-sectional area of the inner diameter of the tube 2, K is a constant related the pressure transducer 3, k is a constant related to elastic forces inside the tube 2 and c is a constant related to the fluid column velocity. An alternative form of the equation above is:

$$\ddot{E} + 2\zeta\omega_n\dot{E} + \omega_n^2 E = \frac{K}{\rho L}p(t)$$

where $\omega_n$ is the natural frequency of the lumen filled tube 2 and pressure transducer 3, and $\zeta$ is the damping ratio of the lumen filled tube 2 and pressure transducer 3.

Accordingly, there is a need for a device and system that can function both as a pressure-sensing device and a guidewire but measures pressure by using a fluid filled lumen inside the guidewire and corrects for the errors that are created when pressure is measured though this fluid filled lumen or tube.

SUMMARY OF THE INVENTION

The present invention is a guidewire that is constructed using tubular members that create a hollow lumen that runs from the proximal end of the guidewire to a window towards the distal end of the wire, where the interior of the tubular member is exposed to the exterior of the tubular member. This internal lumen is filled with a fluid that allows pressure exerted at the window to exert pressure at the proximal end of the guide wire that is proportional to the pressure exerted at the window. This pressure exerted at the proximal end of the guidewire can then be measured using a pressure transducer that is external of the guidewire. The pressure transducer will then convert the pressure at the proximal end of the guidewire to an electrical signal that is proportional to the pressure at the window. The electrical signal is then manipulated to make the pressure measured at the proximal end of the guidewire equal to the pressure exerted at the window, correcting for errors that are due to the pressure signal traveling though the inner lumen of the guidewire.

There are many objects of the present invention in its various embodiments that may be addressed individually or in combinations and permutations. Each embodiment may address one or several of the following objectives.

An object of the invention in one or more embodiments to create device that functions both as a pressure-sensing device and a guidewire.

It is an object of the invention in one or more embodiments to create a device that measures pressure by using a fluid filled lumen inside a guidewire and correct for errors that are created when pressure is measured though this fluid filled lumen.

These and other objects and advantages of the invention will be clear in view of the following description to the invention including the associated drawings.

BRIEF DESCRIPTION OF THE DRAWINGS

The invention will be described hereafter in detail with particular reference to the drawings. Throughout this description, like elements, in whatever embodiment described, refer to common elements wherever referred to and referenced by the same reference number. The characteristics, attributes, functions, interrelations ascribed to a particular element in one locations apply to that element when referred to by the same reference number in another location unless specifically stated otherwise. All Figures are drawn for ease of explanation of the basic teachings of the present invention only; the extensions of the Figures with respect to number, position, relationship and dimensions of the parts to form the preferred embodiment will be explained or will be within the skill of the art after the following description has been read and understood. Further, the exact dimensions and dimensional proportions to conform to specific force, weight, strength and similar requirements will likewise be within the skill of the art after the following description has been read and understood.

DETAILED DESCRIPTION OF THE INVENTION

Figure 2:
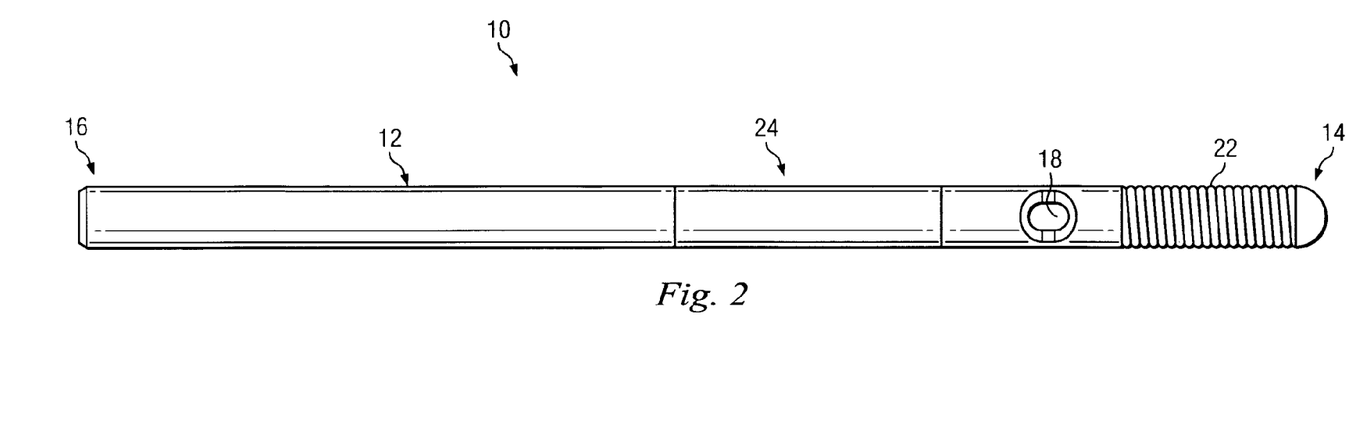
FIG. 2 is a top view of an embodiment of the present invention where the guidewire has a lumen that runs from proximal end to a distal window.

The pressure sensing guidewire of the present invention is shown in FIGS. 2-6 and generally labeled 10. FIG. 2 shows the external surface 12 of the guidewire 10 which also has a distal end 14 and a proximal end 16. Guidewire 10 also has a window 18, located at or near the distal end 14, and an inner lumen 20 that extends from the window 18 to the proximal end 16. The window 18 exposes the external surface 12 of the guidewire 10 to the inner lumen 20 of the guidewire 10. The guidewire 10 has a continuous external surface 12 from the proximal end 16 to the window 18 such that no part of the inner lumen 20 is exposed to the external surface 12 between the proximal end 16 and the window 18. The guidewire 10 has a flexible tip coil 22 and flexible working section 24 that are typical features of a guidewire and consequently well known and understood in the art. The overall diameter of the guidewire 10 is typically 0.014 inches, however the invention is not limited to this dimension. In addition, it is common to keep the outer diameter constant throughout the length of the guidewire 10. But, the invention is not limited to this requirement and there are embodiments of this invention where the outer diameter of the guidewire changes throughout the length of the guidewire.

Figure 3:
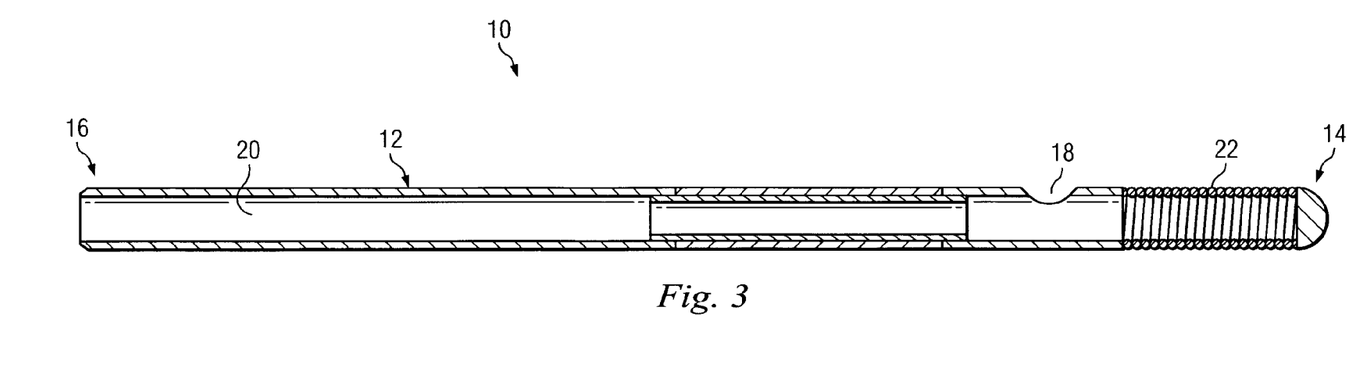
FIG. 3 is a lengthwise cross-sectional view of the guidewire of FIG. 2.

FIG. 3 is the cross-section lengthwise view of the guidewire 10 of FIG. 2. FIG. 3 shows the hollow inner lumen 20 that runs from the proximal end 16 of the guidewire 10 to the window 18. The only points where the inner lumen 20 of the guidewire 10 is exposed to the exterior of the guidewire 10 and surrounding environments is at the proximal end 16 and at the window 18. The window 18 shown in FIGS. 2 and 3 is only one representation of where the window 18 could be located on the guidewire 10. There are many different embodiments of the window 18 location and geometry and this invention is not limited just to the embodiment shown. The inner lumen 20 shown in FIG. 3 that connects the proximal end 16 of the guidewire 10 to the window 18 is filled with a fluid, gel or any media that can transmit the pressure exerted at the window 18 to the proximal end 16 of the guidewire 10. A key feature of the fluid, gel or any other media within the inner lumen 20 is that such fluid, gel or any other media is virtually incompressible in the range of physiological pressures so that pressure applied to the fluid, gel or other material at the window 18 is transferred by the fluid, gel or other material to the proximal end 16 of the guidewire 10.

Figure 4:
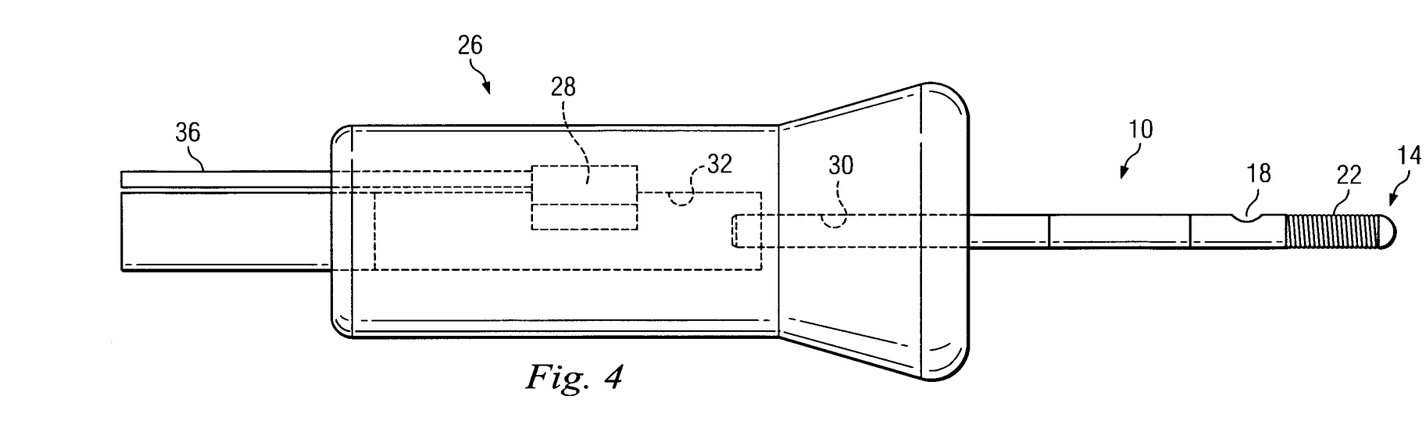
FIG. 4 is a side view of the guidewire in FIG. 2 attached to a pressure transducer housing device.
Figure 5:
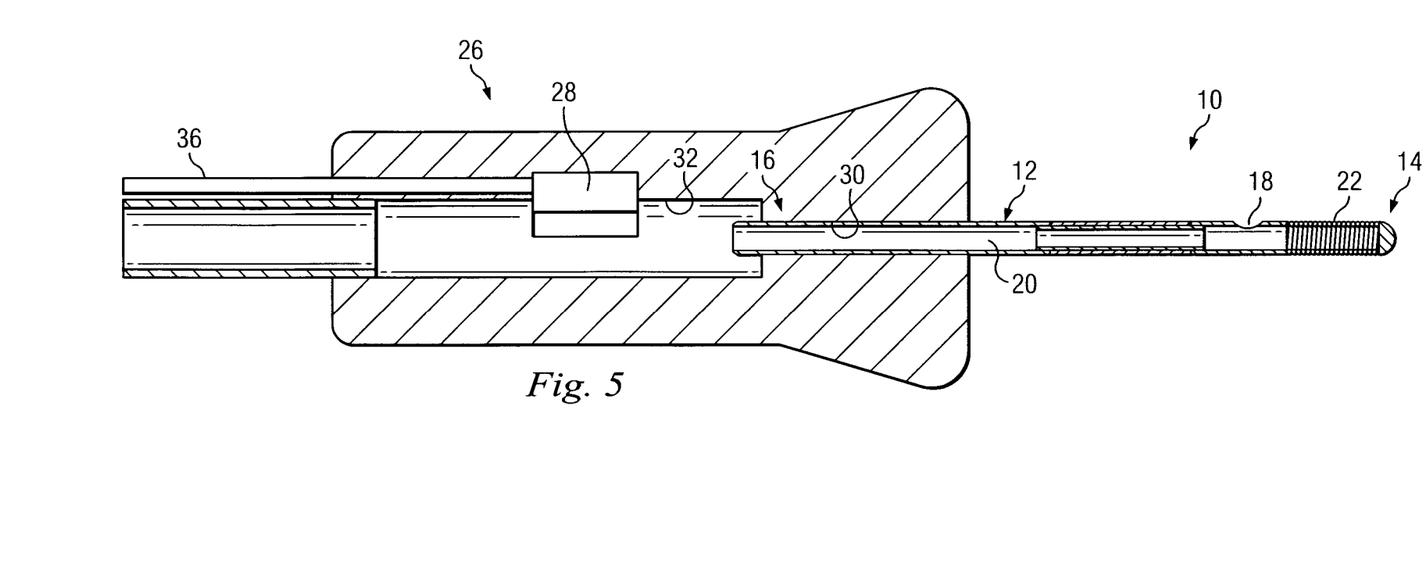
FIG. 5 is a lengthwise cross-sectional view of the arrangement of FIG. 4.

FIG. 4 shows the guidewire 10 shown in FIGS. 2 and 3 mated to a mating device 26 that houses a pressure transducer 28. FIG. 5 shows, in lengthwise cross-section, the mating device 26 of FIG. 4 mated with the guidewire 10. The mating device 26 has a chamber 30 dimensioned to conformally receive and grip the outer surface 12 of the proximal end 16 of the guidewire 10. The mating device 26 contains an inner lumen 32 that is also filled with a fluid, gel or any media that is virtually incompressible at physiological pressures and can transmit pressure and that is in fluid communication with the inner lumen 20 at the proximal end 16 of the guidewire 10. The pressure transducer 28 is in fluid contact with the fluid filled inner lumen 32. The pressure transducer 28 converts mechanical pressure exerted in the fluid filled inner lumen 32 to an electrical signal that is proportional to the pressure of the fluid in the inner lumen 32.

As mentioned above, the mating device 26 attaches to the outer surface 12 of the guidewire 10. In the preferred embodiment of the invention, this attachment is temporary, meaning that the mating device 26 can be easily removed from or attached to the guidewire 10 by the user. However, the present invention is not limited to this feature and the mating device 26, in another embodiment of the invention, is permanently attached to the guidewire 10.

When the mating device 26 is attached to the guidewire 10 by placing the proximal end 16 of the guidewire 10 in the chamber 30, the fluid filled inner lumen 32 and the fluid filled inner lumen 20 are fluidly connected so that there is continuous fluid from the pressure transducer 28 to the window 18 on the guidewire 10. As a result, pressure exerted at the window 18 of the guidewire 10 exerts a pressure on the pressure transducer 28 that is proportional to the pressure exerted at the window 18. The pressure transducer 28 then converts the pressure measured at pressure transducer 28 to an electrical signal that is proportional to the pressure exerted on the fluid at the window 18.

Figures 6, 7:
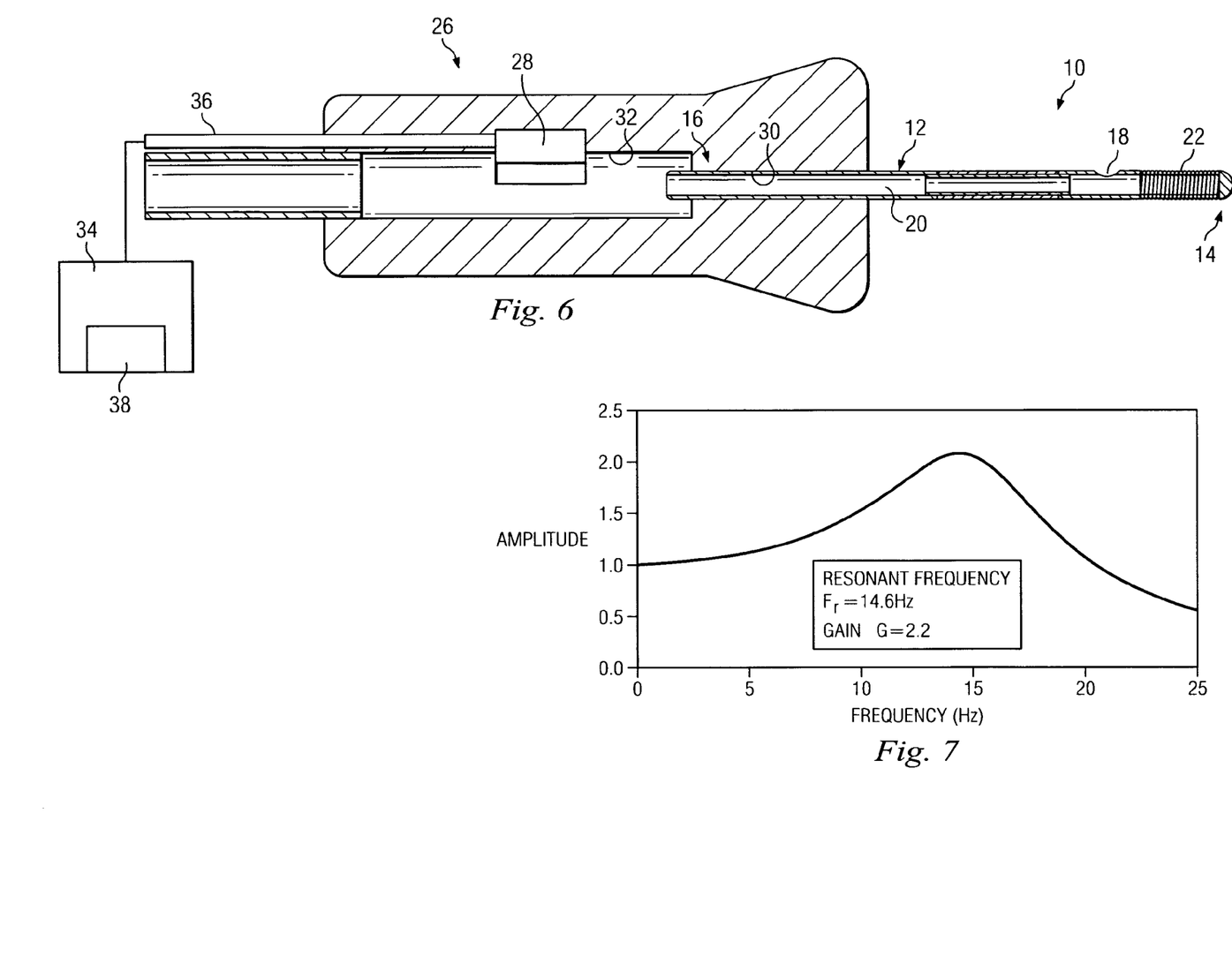
FIG. 6 is a schematic, partial cross-sectional view of an embodiment of the present invention.
FIG. 7 is a chart showing a typical frequency response of fluid within the lumens of the guidewire and mating device of the present invention.

FIG. 6 shows the guidewire 10 of the present invention mated to a mating device 26 that contains a pressure transducer 28 that is in turn connected to a measurement instrument 34 via an electrical connection 36. This measurement instrument 34 reads the electrical signals generated by the pressure transducer 28 that is proportional to the pressure exerted at the window 18 of the guidewire 10 and converts this electrical signal to a pressure reading corresponding to the pressure exerted at the window 18 of the guidewire 10. The measurement instrument 34 conveys this pressure information to a user via a display 38 or by other means of communication well understood in the art or to another medical device or instrument.

In order for the measurement instrument 34 to create a reading that is equal to the pressure exerted at the window 18, the measurement instrument 34 corrects the electrical signal produced by the pressure transducer 28 for distortion and errors caused by the pressure signal traveling though the fluid filled lumens 20, 32 of the guidewire 10 and the mating device 26. These distortions and errors are due to amplification or damping of certain frequencies of the pressure signal as it travels though the fluid filled lumen. As a result the pressure signal measured at the proximal pressure transducer 28 will have a different shape, peak to peak magnitude, and possibly mean pressure compared to what is exerted at the distal window 18. There are many different methods of how this correction can be done and this invention is not limited to the methods that are described here.

One method for correcting for the errors caused to the pressure signal as it travels though the fluid filled lumens 20, 32 of the guidewire 10 and mating device 26, respectively, is to measure the frequency response of the fluid within the lumens 20, 32 with the pressure transducer 28. In order to measure frequency response, a pressure generator is used to create an oscillating pressure signal with a known magnitude and known frequency at the distal window 18. During this time, the pressure is measured by the proximal pressure transducer 28 and its magnitude is compared to the known magnitude of the pressure signal generated at the distal window 18. This process is repeated for all frequencies of interest, which is typically 0-30 Hz for a blood pressure signal. Once this data is collected, the frequency response of the lumen based pressure sensing guidewire can be determined and plotted for the frequencies of interest.

An example of such a frequency response in shown in FIG. 7. In the plot, the Y axis is the magnitude of the pressure measured at the proximal pressure transducer 28 divided by the magnitude of the pressure generated at the distal window 18. The X axis is the frequency of the oscillating pressure signal generated at the distal window 18. Once the frequency response is known, the pressure measured by pressure transducer 28 is corrected so that it measures more precisely the pressure at the window 18 of the guidewire 10.

In order to do this, the pressure measured at the proximal pressure transducer 28 has to be converted into the frequency domain using a version of a Fourier transform or any method that decomposes a signal into its constituent frequencies. Once in the frequency domain, the signal can be scaled based on the measured frequency response such that the magnitude of the measured signal at the proximal pressure transducer 28 equals the magnitude of pressure exerted at the distal window 18, at a given frequency. Once this is done for all frequencies of interest, the scaled frequency domain signal is converted back into the time domain and the result is a time domain pressure signal that is measured at the proximal transducer 28 but is equal to the pressure exerted at the distal window 18.

Another method of corrected the pressure measured by the pressure transducer 28 for distortions and errors is to correct for these distortions and errors by comparing the pressure measured by the pressure transducer 28 attached to the guidewire 10 to another pressure transducer in the body, a so called "Reference Transducer," that is measuring the same pressure that is exerted at the guidewire 10's window 18. The reference transducer can be placed anywhere in the body's vasculature (e.g., at or near the end of the guide catheter, typically at the start of the coronary tree) as long as the window 18 of the guidewire 10 is at or near the same location as where the reference transducer is measuring and where there is a pulsatile signal due to the heart beat.

Since blood pressure in the body is pulsatile, the scale of the pressure measured by the pressure transducer 28 attached to the guidewire 10 can be corrected by determining the scale factor required to make the peak to peak signal measured by the pressure transducer 28 equal to the peak to peak signal measured by the Reference Transducer. Offset for the pressure transducer 28 can be corrected by making the mean pressure measured by the pressure transducer 28 equal to the mean pressure measured by the Reference Transducer. Once the pressure transducer 28 is equalized to the Reference Transducer, the guidewire 10 can be positioned in any artery or vein of the body, including those into which the Reference Transducer cannot fit, and measure the pressure there accurately.

Another method to correct for these distortions and errors is to compare the frequency domain of the pressure measured by the pressure transducer 28 to the frequency domain of the Reference Transducer that is measuring the same pressure exerted at the guidewire 10's window 18. A Fourier Transform or FFT (Fast Fourier Transform) is performed on the pressure data measured by the pressure transducer 28 and compared to the Fourier Transform or FFT of the pressure data from the Reference Transducer. At each frequency, the data from the pressure transducer 28 is scaled so that the magnitude at the frequency is equal to the magnitude of the pressure data from the Reference Transducer at the same frequency. By determining the correct scale values at each frequency, a transfer function is then created where data from the pressure transducer 28 is adjusted in the frequency domain by the appropriate scale value and then converted back to the time domain so that the resulting pressure data is equal to the time domain pressure signal of the Reference Transducer. Once this transfer function is determined, the guidewire 10 can be positioned in any artery or vein of the body, including where the Reference Transducer cannot fit, and measure the pressure there accurately.

The present invention has been described in connection with several different embodiments. The present invention also anticipates that more than one embodiment or correction method may be applied or combined into a single device. Further, although the window 18 has been shown as being directed radially from the inner lumen 20, the window 18 may be directed axially at the distal end 14. Further, more than one window 18 may be present wherever located.

The present invention has been described in connection with certain embodiments, combinations, configurations and relative dimensions. It is to be understood, however, that the description given herein has been given for the purpose of explaining and illustrating the invention and are not intended to limit the scope of the invention. In addition, it is clear than an almost infinite number of minor variations to the form and function of the disclosed invention could be made and also still be within the scope of the invention. Consequently, it is not intended that the invention be limited to the specific embodiments and variants of the invention disclosed. It is to be further understood that changes and modifications to the descriptions given herein will occur to those skilled in the art. Therefore, the scope of the invention should be limited only by the scope of the claims.

What is claimed is:

1. A guidewire system, comprising:
a guidewire including a distal end, a proximal end, an external surface, and a window located at or near the distal end, the guidewire having an inner lumen that extends from the window to the proximal end wherein the window exposes the external surface of the guidewire to the inner lumen of the guidewire, the external surface being continuous from the proximal end to the window so that no part of the inner lumen is exposed to the external surface between the proximal end and the window;
a mating device having an inner lumen that is filled with a fluid, gel or any media that is virtually incompressible at physiological pressures and can transmit pressure and that is in fluid communication with the inner lumen at the proximal end of the guidewire, the mating device also having a chamber dimensioned to conformally receive and grip the outer surface of the proximal end of the guidewire;
a pressure transducer in fluid contact with the fluid filled inner lumen of the mating device wherein the pressure transducer converts mechanical pressure exerted in the fluid filled inner lumen of the mating device to an electrical signal that is proportional to the pressure of the fluid in the inner lumen of the mating device;
whereby, when the mating device is attached to the guidewire by placing the proximal end of the guidewire in the chamber, the fluid filled inner lumen of the mating device and the fluid filled inner lumen of the guidewire are fluidly connected so that there is a continuous fluid from the pressure transducer to the window on the guidewire so that pressure exerted at the window of the guidewire exerts a pressure on the pressure transducer that is proportional to the pressure exerted at the window;
whereby the pressure transducer then converts the pressure measured at pressure transducer to an electrical signal that is proportional to the pressure exerted on the fluid at the window;
a measurement instrument electrically connected to the pressure transducer wherein the measurement instrument reads the electrical signals generated by the pressure transducer that is proportional to the pressure exerted at the window of the guidewire and converts this electrical signal to a pressure reading corresponding to the pressure exerted at the window of the guidewire; and
a display and wherein the measurement instrument conveys the pressure information to a user via the display;
wherein the guidewire system is configured to correct the electrical signal produced by the pressure transducer for distortions and errors caused by the pressure signal traveling through the fluid filled lumens of the guidewire and the mating device by:
creating an oscillating pressure signal with a known magnitude and known frequency at the distal window;
measuring the pressure by the pressure transducer;
comparing the pressure measured by the pressure transducer to the known magnitude of the pressure signal generated at the distal window by the oscillating pressure signal to create an offset magnitude for that frequency;
repeating this process for all frequencies of interest; and
applying the offset magnitude to the pressure measured by the guidewire in use for each frequency.

2. The guidewire of claim 1 wherein the frequency range of frequencies of interest is about 0-30 Hz.

3. A guidewire system, comprising:
a guidewire including a distal end, a proximal end, an external surface, and a window located at or near the distal end, the guidewire having an inner lumen that extends from the window to the proximal end wherein the window exposes the external surface of the guidewire to the inner lumen of the guidewire, the external surface being continuous from the proximal end to the window so that no part of the inner lumen is exposed to the external surface between the proximal end and the window;
a mating device having an inner lumen that is filled with a fluid, gel or any media that is virtually incompressible at physiological pressures and can transmit pressure and that is in fluid communication with the inner lumen at the proximal end of the guidewire, the mating device also having a chamber dimensioned to conformally receive and grip the outer surface of the proximal end of the guidewire;
a pressure transducer in fluid contact with the fluid filled inner lumen of the mating device wherein the pressure transducer converts mechanical pressure exerted in the fluid filled inner lumen of the mating device to an electrical signal that is proportional to the pressure of the fluid in the inner lumen of the mating device;
whereby, when the mating device is attached to the guidewire by placing the proximal end of the guidewire in the chamber, the fluid filled inner lumen of the mating device and the fluid filled inner lumen of the guidewire are fluidly connected so that there is a continuous fluid from the pressure transducer to the window on the guidewire so that pressure exerted at the window of the guidewire exerts a pressure on the pressure transducer that is proportional to the pressure exerted at the window;
whereby the pressure transducer then converts the pressure measured at pressure transducer to an electrical signal that is proportional to the pressure exerted on the fluid at the window;
a measurement instrument electrically connected to the pressure transducer wherein the measurement instrument reads the electrical signals generated by the pressure transducer that is proportional to the pressure exerted at the window of the guidewire and converts this electrical signal to a pressure reading corresponding to the pressure exerted at the window of the guidewire; and
a display and wherein the measurement instrument conveys the pressure information to a user via the display;
wherein the guidewire system is configured to correct the electrical signal produced by the pressure transducer for distortions and errors caused by the pressure signal traveling through the fluid filled lumens of the guidewire and the mating device by:
providing a reference transducer;
placing the reference transducer in a body's vasculature so that the window of the guidewire is at or near the same location as where the reference transducer is measuring and where there is a pulsatile signal due to the heart beat;
taking a pressure reading with the reference transducer;
correcting the scale of the pressure measured by the pressure transducer attached to the guidewire by determining the scale factor required to make the peak to peak signal measured by the pressure transducer equal to the peak to peak signal measured by the reference transducer; and applying the scale factor to the pressure measured by the pressure transducer so that the mean pressure measured by the pressure transducer is equal to the mean pressure measured by the reference transducer.

4. A guidewire system, comprising:

a guidewire including a distal end, a proximal end, an external surface, and a window located at or near the distal end, the guidewire having an inner lumen that extends from the window to the proximal end wherein the window exposes the external surface of the guidewire to the inner lumen of the guidewire, the external surface being continuous from the proximal end to the window so that no part of the inner lumen is exposed to the external surface between the proximal end and the window;

a mating device having an inner lumen that is filled with a fluid, gel or any media that is virtually incompressible at physiological pressures and can transmit pressure and that is in fluid communication with the inner lumen at the proximal end of the guidewire, the mating device also having a chamber dimensioned to conformally receive and grip the outer surface of the proximal end of the guidewire;

a pressure transducer in fluid contact with the fluid filled inner lumen of the mating device wherein the pressure transducer converts mechanical pressure exerted in the fluid filled inner lumen of the mating device to an electrical signal that is proportional to the pressure of the fluid in the inner lumen of the mating device;

whereby, when the mating device is attached to the guidewire by placing the proximal end of the guidewire in the chamber, the fluid filled inner lumen of the mating device and the fluid filled inner lumen of the guidewire are fluidly connected so that there is a continuous fluid from the pressure transducer to the window on the guidewire so that pressure exerted at the window of the guidewire exerts a pressure on the pressure transducer that is proportional to the pressure exerted at the window;

whereby the pressure transducer then converts the pressure measured at pressure transducer to an electrical signal that is proportional to the pressure exerted on the fluid at the window;

a measurement instrument electrically connected to the pressure transducer wherein the measurement instrument reads the electrical signals generated by the pressure transducer that is proportional to the pressure exerted at the window of the guidewire and converts this electrical signal to a pressure reading corresponding to the pressure exerted at the window of the guidewire; and a display and wherein the measurement instrument conveys the pressure information to a user via the display;

wherein the guidewire system is configured to correct the electrical signal produced by the pressure transducer for distortions and errors caused by the pressure signal traveling through the fluid filled lumens of the guidewire and the mating device by comparing the frequency domain of the pressure measured by the pressure transducer to the frequency domain of the reference transducer that is measuring the same pressure exerted at the guidewire's window, including:

performing a Fourier Transform or Fast Fourier Transform on the pressure data measured by the pressure transducer;

performing a Fourier Transform or Fast Fourier Transform of the pressure data from the reference transducer;

scaling, at each frequency of interest, the data from the pressure transducer so that the magnitude at the frequency is equal to the magnitude of the pressure data from the reference transducer at the same frequency;

creating a transfer function based on the correct scale values at each frequency so that the data from the pressure transducer is adjusted in the frequency domain by the appropriate scale value and then converted back to the time domain so that the resulting pressure data is equal to the time domain pressure signal of the reference transducer; and applying the transfer function to the pressure measured by the pressure transducer.

5. A method of correcting an electrical signal for distortions and errors caused by the pressure signal traveling through fluid filled lumens where the electrical signal is produced by a pressure transducer in a pressure sensing device comprising:

a guidewire having a distal end, a proximal end, an external surface and a window located at or near the distal end, the guidewire having an inner lumen that extends from the window to the proximal end wherein the window exposes the external surface of the guidewire to the inner lumen of the guidewire, the external surface being continuous from the proximal end to the window so that no part of the inner lumen is exposed to the external surface between the proximal end and the window;

wherein the inner lumen is filled with a fluid, gel or any media that can transmit the pressure exerted at the window to the proximal end of the guidewire; and further comprising:

a mating device having an inner lumen that is filled with a fluid, gel or any media that is virtually incompressible at physiological pressures and can transmit pressure and that is in fluid communication with the inner lumen at the proximal end of the guidewire, the mating device also having a chamber dimensioned to conformally receive and grip the outer surface of the proximal end of the guidewire;

a pressure transducer in fluid contact with the fluid filled inner lumen of the mating device wherein the pressure transducer converts mechanical pressure exerted in the fluid filled inner lumen of the mating device to an electrical signal that is proportional to the pressure of the fluid in the inner lumen of the mating device;

whereby, when the mating device is attached to the guidewire by placing the proximal end of the guidewire in the chamber, the fluid filled inner lumen of the mating device and the fluid filled inner lumen of the guidewire are fluidly connected so that there is a continuous fluid from the pressure transducer to the window on the guidewire so that pressure exerted at the window of the guidewire exerts a pressure on the pressure transducer that is proportional to the pressure exerted at the window;

whereby the pressure transducer then converts the pressure measured at pressure transducer to an electrical signal that is proportional to the pressure exerted on the fluid at the window;

the method comprising the steps of:

creating an oscillating pressure signal with a known magnitude and known frequency at the distal window;

measuring the pressure by the pressure transducer;

comparing the pressure measured by the pressure transducer to the known magnitude of the pressure signal generated at the distal window by the oscillating pressure signal to create an offset magnitude for that frequency;

repeating this process for all frequencies of interest;

applying the offset magnitude to the pressure measured by the guidewire in use for each frequency.

6. A method of correcting an electrical signal for distortions and errors caused by the pressure signal traveling through fluid filled lumens where the electrical signal is produced by a pressure transducer in a pressure sensing device comprising:

a guidewire having a distal end, a proximal end, an external surface and a window located at or near the distal end, the guidewire having an inner lumen that extends from the window to the proximal end wherein the window exposes the external surface of the guidewire to the inner lumen of the guidewire, the external surface being continuous from the proximal end to the window so that no part of the inner lumen is exposed to the external surface between the proximal end and the window;

wherein the inner lumen is filled with a fluid, gel or any media that can transmit the pressure exerted at the window to the proximal end of the guidewire; and further comprising:

a mating device having an inner lumen that is filled with a fluid, gel or any media that is virtually incompressible at physiological pressures and can transmit pressure and that is in fluid communication with the inner lumen at the proximal end of the guidewire, the mating device also having a chamber dimensioned to conformally receive and grip the outer surface of the proximal end of the guidewire;

a pressure transducer in fluid contact with the fluid filled inner lumen of the mating device wherein the pressure transducer converts mechanical pressure exerted in the fluid filled inner lumen of the mating device to an electrical signal that is proportional to the pressure of the fluid in the inner lumen of the mating device;

whereby, when the mating device is attached to the guidewire by placing the proximal end of the guidewire in the chamber, the fluid filled inner lumen of the mating device and the fluid filled inner lumen of the guidewire are fluidly connected so that there is a continuous fluid from the pressure transducer to the window on the guidewire so that pressure exerted at the window of the guidewire exerts a pressure on the pressure transducer that is proportional to the pressure exerted at the window;

whereby the pressure transducer then converts the pressure measured at pressure transducer to an electrical signal that is proportional to the pressure exerted on the fluid at the window;

the method comprising the steps of:

providing a reference transducer;

placing the reference transducer in a body's vasculature so that the window of the guidewire is at or near the same location as where the reference transducer is measuring and where there is a pulsatile signal due to the heart beat;

taking a pressure reading with the reference transducer;

correcting the scale of the pressure measured by the pressure transducer attached to the guidewire by determining the scale factor required to make the peak to peak signal measured by the pressure transducer equal to the peak to peak signal measured by the reference transducer;

and applying the scale factor to the pressure measured by the pressure transducer so that the mean pressure measured by the pressure transducer is equal to the mean pressure measured by the reference transducer.

7. A method of correcting an electrical signal for distortions and errors caused by the pressure signal traveling through fluid filled lumens where the electrical signal is produced by a pressure transducer in a pressure sensing device comprising:

a guidewire having a distal end, a proximal end, an external surface and a window located at or near the distal end, the guidewire having an inner lumen that extends from the window to the proximal end wherein the window exposes the external surface of the guidewire to the inner lumen of the guidewire, the external surface being continuous from the proximal end to the window so that no part of the inner lumen is exposed to the external surface between the proximal end and the window;

wherein the inner lumen is filled with a fluid, gel or any media that can transmit the pressure exerted at the window to the proximal end of the guidewire; and further comprising:

a mating device having an inner lumen that is filled with a fluid, gel or any media that is virtually incompressible at physiological pressures and can transmit pressure and that is in fluid communication with the inner lumen at the proximal end of the guidewire, the mating device also having a chamber dimensioned to conformally receive and grip the outer surface of the proximal end of the guidewire;

a pressure transducer in fluid contact with the fluid filled inner lumen of the mating device wherein the pressure transducer converts mechanical pressure exerted in the fluid filled inner lumen of the mating device to an electrical signal that is proportional to the pressure of the fluid in the inner lumen of the mating device;

whereby, when the mating device is attached to the guidewire by placing the proximal end of the guidewire in the chamber, the fluid filled inner lumen of the mating device and the fluid filled inner lumen of the guidewire are fluidly connected so that there is a continuous fluid from the pressure transducer to the window on the guidewire so that pressure exerted at the window of the guidewire exerts a pressure on the pressure transducer that is proportional to the pressure exerted at the window;

whereby the pressure transducer then converts the pressure measured at pressure transducer to an electrical signal that is proportional to the pressure exerted on the fluid at the window;

the method comprising the steps of:

performing a Fourier Transform or Fast Fourier Transform on the pressure data measured by the pressure transducer;

performing a Fourier Transform or Fast Fourier Transform of the pressure data from the reference transducer;

scaling, at each frequency of interest, the data from the pressure transducer so that the magnitude at the frequency is equal to the magnitude of the pressure data from the reference transducer at the same frequency;

creating a transfer function based on the correct scale values at each frequency so that the data from the pressure transducer is adjusted in the frequency domain by the appropriate scale value and then converted back to the time domain so that the resulting pressure data is equal to the time domain pressure signal of the reference transducer; and applying the transfer function to the pressure measured by the pressure transducer.

8. A pressure-sensing intravascular guidewire system, comprising:
- a guidewire body having a proximal portion, a distal portion, an opening at the distal portion, and an inner lumen in fluid communication with the opening, the inner lumen extending from the opening to the proximal portion;
- a mating device configured to receive the proximal portion of the guidewire body, the mating device having an inner lumen that is in fluid communication with the inner lumen of the guidewire body when the proximal portion of the guidewire body is received by the mating device, wherein the inner lumen of the mating device is filled with a media configured to transmit pressure from the inner lumen of the guidewire body to a pressure transducer in fluid communication with the inner lumen of the mating device such that the pressure transducer outputs an electrical signal that is proportional to a pressure at the opening of the guidewire body; and
- a measurement instrument in communication with the pressure transducer such that the measurement instrument reads the electrical signal generated by the pressure transducer that is proportional to the pressure at the opening of the guidewire body and converts the electrical signal to a pressure reading corresponding to the pressure at the opening of the guidewire;
- wherein the measurement instrument is configured to convert the electrical signal to a pressure reading corresponding to the pressure at the opening of the guidewire by applying a transfer function correlating pressure measurements of the pressure transducer to pressure measurements of the reference pressure transducer and wherein the transfer function is determined by correlating the pressure measurements of the pressure transducer to the pressure measurements of the reference pressure transducer at a plurality of frequencies.

9. The pressure-sensing intravascular guidewire system of claim 8, wherein the guidewire has an outer diameter of approximately 0.014 inches.

10. The pressure-sensing intravascular guidewire system of claim 8, wherein the guidewire includes a flexible tip coil.

11. The pressure-sensing intravascular guidewire system of claim 8, wherein the mating device is permanently attached to the guidewire.

12. The pressure-sensing intravascular guidewire system of claim 8, wherein the mating device is temporarily attachable to the guidewire.

13. The pressure-sensing intravascular guidewire system of claim 8, wherein the plurality of frequencies include frequencies between 0-30 Hz.

14. A pressure-sensing intravascular guidewire system, comprising:
- a guidewire body having a proximal portion, a distal portion, an opening at the distal portion, and an inner lumen in fluid communication with the opening, the inner lumen extending from the opening to the proximal portion;
- a mating device configured to receive the proximal portion of the guidewire body, the mating device having an inner lumen that is in fluid communication with the inner lumen of the guidewire body when the proximal portion of the guidewire body is received by the mating device, wherein the inner lumen of the mating device is filled with a media configured to transmit pressure from the inner lumen of the guidewire body to a pressure transducer in fluid communication with the inner lumen of the mating device such that the pressure transducer outputs an electrical signal that is proportional to a pressure at the opening of the guidewire body; and
- a measurement instrument in communication with the pressure transducer such that the measurement instrument reads the electrical signal generated by the pressure transducer that is proportional to the pressure at the opening of the guidewire body and converts the electrical signal to a pressure reading corresponding to the pressure at the opening of the guidewire, wherein the measurement instrument is configured to convert the electrical signal to a pressure reading corresponding to the pressure at the opening of the guidewire by applying the offset magnitude correlating pressure measurements of the pressure transducer to the oscillating pressure signal with the known magnitude and known frequency for one or more frequencies of interest and wherein the one or more frequencies of interest are between 0-30 Hz.

* * * * *